United States Patent
Hirota et al.

(10) Patent No.: US 6,649,343 B1
(45) Date of Patent: Nov. 18, 2003

(54) DNA CHIP AND METHOD FOR PRODUCING THE SAME

(75) Inventors: Toshikazu Hirota, Nagoya (JP); Takao Ohnishi, Nagoya (JP); Yukihisa Takeuchi, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 41 days.

(21) Appl. No.: 09/693,228

(22) Filed: Oct. 20, 2000

(65) Prior Publication Data (65)

(30) Foreign Application Priority Data

Oct. 22, 1999 (JP) .............................. 11-301627
Mar. 28, 2000 (JP) ........................ 2000-089971

(51) Int. Cl.[7] .............................. C12Q 1/68; C12M 1/36; G01N 15/06; C07H 21/04
(52) U.S. Cl. ..................... 435/6; 435/283.1; 435/287.2; 435/287.3; 435/288.4; 422/68.1; 422/100; 536/24.3
(58) Field of Search ................... 422/100, 68.1; 435/6, 287.2, 288.4, 287.3, 283.1; 536/24.3

(56) References Cited

U.S. PATENT DOCUMENTS

| 5,486,337 | A | * | 1/1996 | Ohkawa ..................... 422/100 |
| 5,677,195 | A | * | 10/1997 | Winkler et al. ............. 436/518 |
| 6,004,752 | A | * | 12/1999 | Loewy et al. | |
| 6,099,803 | A | * | 8/2000 | Ackley et al. ............. 422/68.1 |
| 6,362,004 | B1 | * | 3/2002 | Noblett | |

FOREIGN PATENT DOCUMENTS

| JP | 6-040030 A | 2/1994 |
| JP | 8-201265 A | 8/1996 |

* cited by examiner

Primary Examiner—B. J. Forman
(74) Attorney, Agent, or Firm—Burr & Brown

(57) ABSTRACT

A DNA chip includes a large number of minute spots formed by dripping sample solutions onto a base plate. The base plate is provided with positional deviation-correcting means for displacing the spots and automatically correcting any positional deviation of each of the spots. The positional deviation-correcting means includes any one of at least one projection, at least one recess and electric field-generating means for providing charged states on the base plate centered at a correct position for each of the spots supplied on the base plate.

5 Claims, 19 Drawing Sheets

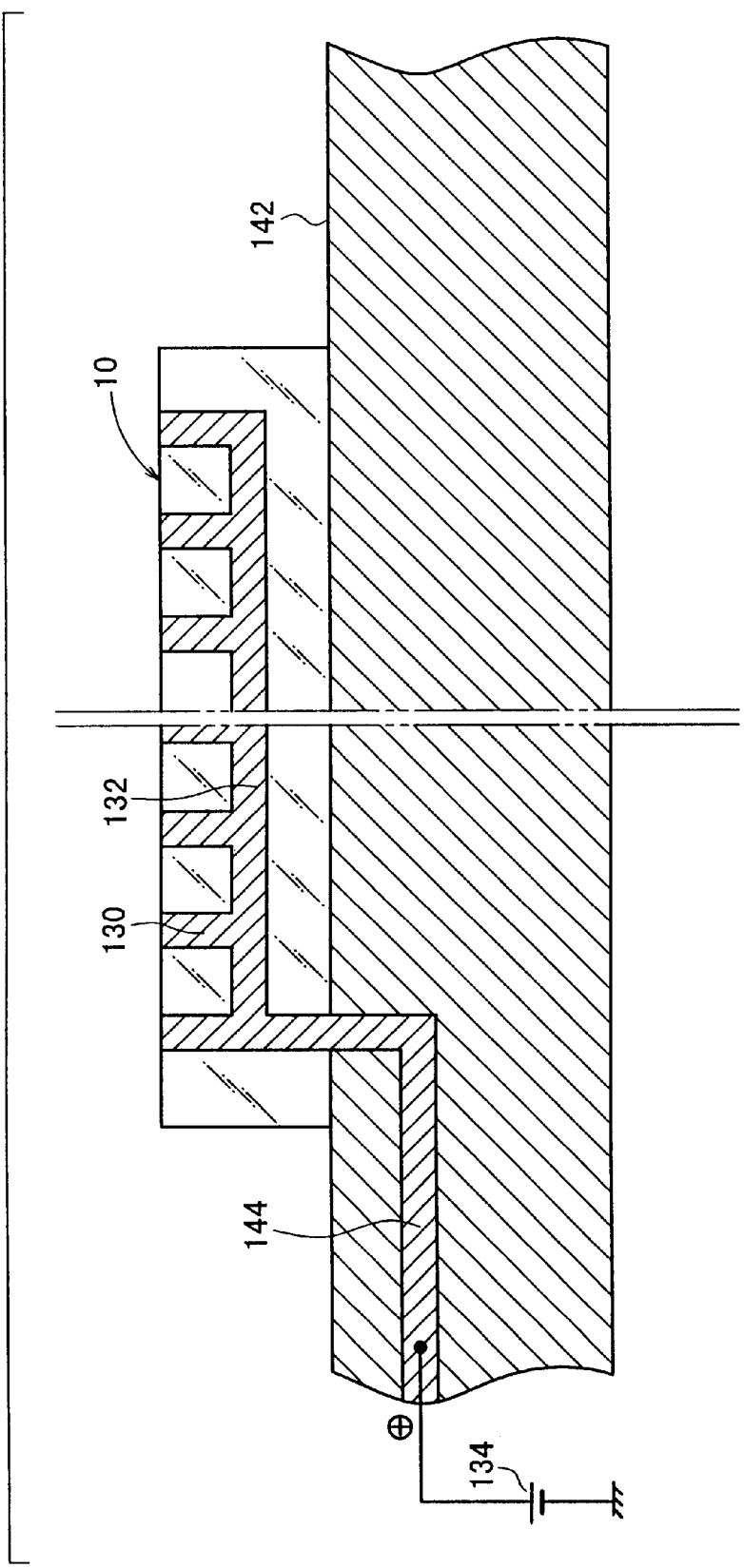

DNA CHIP AND METHOD FOR PRODUCING THE SAME

BACKGROUND OF THE INVENTION

1. Field of the Invention

The present invention relates to a DNA chip (DNA microarray) in which several thousands to not less than ten thousands kinds of different types of DNA fragments are aligned and fixed as minute spots at a high density on a base plate such as a microscopic slide glass, and a method for producing the same.

2. Description of the Related Art

The method for analyzing the genetic structure has been remarkably progressed in recent years. A large number of genetic structures represented by those of human gene have been clarified. The analysis of the genetic structure as described above uses a DNA chip (DNA microarray) in which several thousands to not less than ten thousands kinds of different types of DNA fragments are aligned and fixed as minute spots on a base plate such as a microscopic slide glass.

Those widely used as a method for forming the minute spots in the production of the DNA chip are based on a system such as the QUILL system, the pin & ring system, and the spring pin system in which a sample solution containing DNA fragments is supplied in a contact manner onto the base plate by using a so-called pin. Even when any one of the foregoing methods is adopted, it is important to suppress the dispersion of the volume and the shape of each of the minute spots to be low so that the distance between the respective minute spots is maintained to be constant.

On the other hand, in order to realize a higher density, it is also greatly expected to develop a new method in which the shape control performance is satisfactory for the minute spot, and the productivity is excellent.

When the large number of minute spots are formed on the base plate by supplying (including dripping) the sample solution, a dispenser is used, in which a large number of supply nozzles (for example, pins or spring pins) are arranged, for example, in a matrix form.

Usually, the arrangement pitch of the supply nozzles is larger than the arrangement pitch of the minute spots to be formed on the base plate. Therefore, the sample solution is supplied while deviating the supply position for the dispenser.

During this process, if any dispersion arises in the deviation width for the dispenser or in the arrangement pitch of the supply nozzles, it is feared that the dispersion is directly reflected on the arrangement state of the minute spots, and the adjoining spots are merged to one another to form one spot.

On the other hand, a procedure has been also investigated, in which the spotting is performed by using the so-called ink-jet system which is practically used for printers. However, if a supply apparatus based on the ink-jet system is used, it is feared that the adjoining spots are merged to one another to form one spot, for example, due to the influence of the so-called traveling curvature in which the direction of the discharged droplets is bent, and the unnecessary discharged droplets called satellites.

SUMMARY OF THE INVENTION

The present invention has been made taking the foregoing problems into consideration, an object of which is to provide a DNA chip which makes it possible to realize a state in which the arrangement state of a large number of minute spots to be formed on a base plate conforms to a prescribed arrangement pitch, even when any dispersion occurs in the deviation width of a dispenser or the arrangement pitch of supply nozzles, and even when any positional deviation of discharged droplets occurs due to the traveling curvature or the satellites when a supply apparatus based on the ink-jet system is used.

Another object of the present invention is to provide a method for producing a DNA chip, which makes it possible to realize a state in which the arrangement state of a large number of minute spots to be formed on a base plate conforms to a prescribed arrangement pitch, even when any dispersion occurs in the deviation width of a dispenser or the arrangement pitch of supply nozzles, and even when any positional deviation of discharged droplets occurs due to the traveling curvature or the satellites when a supply apparatus based on the ink-jet system is used, making it possible to improve the quality of the DNA chip and improve the yield.

According to the present invention, there is provided a DNA chip comprising a large number of minute spots formed by supplying sample solutions onto a base plate; wherein the base plate is provided with a positional deviation-correcting means for automatically correcting any positional deviation of the minute spot.

Accordingly, when the sample solution is supplied onto the base plate, even if the supply position is deviated from a prescribed position, then the minute spot to be formed by supplying the sample solution is moved to the prescribed position by the aid of the positional deviation-correcting means. Thus, the positional deviation is corrected.

As described above, according to the DNA chip concerning the present invention, it is possible to realize a state in which the arrangement state of the large number of minute spots to be formed on the base plate conforms to a prescribed arrangement pitch, even when any dispersion occurs in the deviation width of a dispenser or the arrangement pitch of supply nozzles, and even when any positional deviation of discharged droplets occurs due to the traveling curvature or the satellites when a supply apparatus based on the ink-jet system is used.

According to another aspect of the present invention, there is provided a method for producing a DNA chip by supplying a large number of sample solutions onto a base plate; comprising the step of using, as the base plate, a base plate provided with a positional deviation-correcting means for automatically correcting any positional deviation of the minute spot to produce the DNA chip.

Accordingly, it is possible to realize a state in which the arrangement state of the large number of minute spots to be formed on the base plate conforms to a prescribed arrangement pitch, even when any dispersion occurs in the deviation width of a dispenser or the arrangement pitch of supply nozzles, and even when any positional deviation of discharged droplets occurs due to the traveling curvature or the satellites when a supply apparatus based on the ink-jet system is used, making it possible to improve the quality of the DNA chip and improve the yield.

It is preferable that the sample solution is supplied by using a supply apparatus based on the ink-jet system. In this case, it is preferable that the supply apparatus is a dispenser comprising a plurality of arranged micropipettes each including a pouring port for pouring the sample solution from the outside, a cavity for pouring and charging the sample solution thereinto, and a discharge port for discharging the sample solution, formed on at least one or more substrates, the micropipette further including a piezoelectric/electrostrictive element disposed on at least one wall surface of the substrate which forms the cavity so that the sample solution is movable in the cavity, and mutually different types of the sample solutions being discharged from the discharge ports of the respective micropipettes. Further, it is more preferable that the sample solution is moved in a laminar flow.

When the ink-jet system is used, then the minute spot can be formed at a high speed, and it is possible to freely set the speed and the liquid amount of the discharged droplets. Therefore, the following advantages are obtained. That is, it is possible to correctly form the minute spot with the prescribed liquid amount and/or with the shape. The dispersion between the respective minute spots is decreased as compared with a system in which the operation is performed with a pin or a spring pin.

Unlike the pin system, the minute spot is formed in a non-contact manner in the ink-jet system. Therefore, there is neither physical interference nor contact with respect to the positional deviation-correcting means. Thus, the ink-jet system can be preferably used.

Concerning the degree of freedom of the design, for example, of the spot amount and the discharge speed, possessed by the ink-jet system, another advantage is obtained such that it is easy to effect the matching with the positional deviation-correcting means. That is, the following advantage is obtained. When the correction is to be made to a great extent due to a large positional deviation amount, the contact with the positional deviation-correcting means may be facilitated, for example, by increasing the discharge amount and the discharge speed to enlarge the spread of the spot on the base plate. Thus, it is possible to perform the correction of the positional deviation in a reliable manner.

It is also preferable that the positional deviation-correcting means is a projection formed at a position at which the minute spot is to be formed on the base plate, or the positional deviation-correcting means is constructed by a hydrophilic zone formed at a position at which the minute spot is to be formed, and a water-repellent zone formed at the other portions on the base plate.

It is also preferable that the positional deviation-correcting means is a recess formed at a position at which the minute spot is to be formed on the base plate, or the positional deviation-correcting means is constructed by providing different surface state for a portion at which the minute spot is to be formed and the other portions on the base plate.

It is also preferable that the positional deviation-correcting means includes an electric field-generating means for providing a charged state of a portion at which the minute spot is to be formed, the charged state being opposite to that of the sample solution on the base plate.

For example, the electric field-generating means is operated as follows. That is, when the sample solution is negatively charged (minus charge), if the portion, at which the minute spot is to be formed, is allowed to have the charged state opposite to that of the sample solution, i.e., the positive charged state (state of plus charge), then the spotting can be reliably performed at the prescribed position, which is preferred. When the sample solution is in the state of plus charge, the portion, at which the minute spot is to be formed, may be in the state of minus charge.

Further, when the ink-jet system is used as the system for supplying the sample solution, the minute spot can be formed in a non-contact manner. Therefore, the discharge direction of droplets is aligned with the direction of the electric field. Further, the correction is easily made for the dripping position by the aid of the electric field. Therefore, this system can be preferably used.

When the sample solution is a solution containing the DNA fragment, the following procedure is preferred in order to obtain a more effective positional deviation-correcting effect by the electric field. That is, a functional group for adding the charge is added to the DNA fragment, or the DNA fragment is dispersed in a solution having charge.

The above and other objects, features, and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 18 shows a sectional view illustrating a positional deviation-correcting means according to an eighth modified embodiment;

DESCRIPTION OF THE PREFERRED EMBODIMENTS

Exemplary embodiments of the DNA chip and the method for producing the same according to the present invention will be explained below with reference to FIGS. 1 to 19B.

Figure 1:
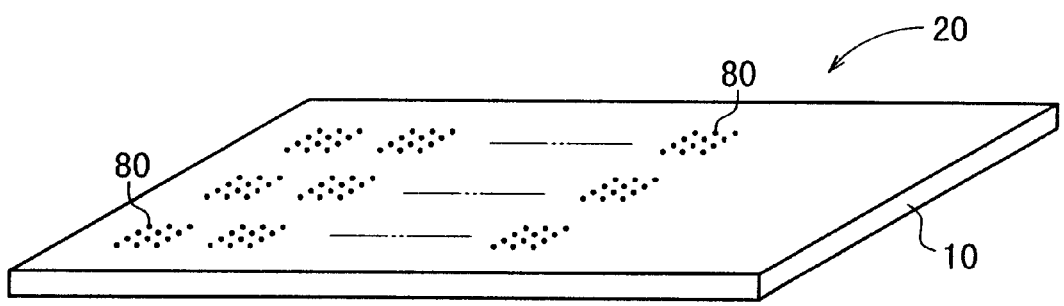
FIG. 1 shows a perspective view illustrating a DNA chip according to an embodiment of the present invention (DNA chip produced by a production method according to the embodiment of the present invention)

As shown in FIG. 1, a DNA chip 20 according to an embodiment of the present invention comprises a large number of arranged minute spots 80 constructed by supplying (including dripping) a sample solution onto a base plate 10. Especially, a positional deviation-correcting means for automatically correcting the positional deviation of the minute spot 80 is provided on the base plate 10.

Figure 2:
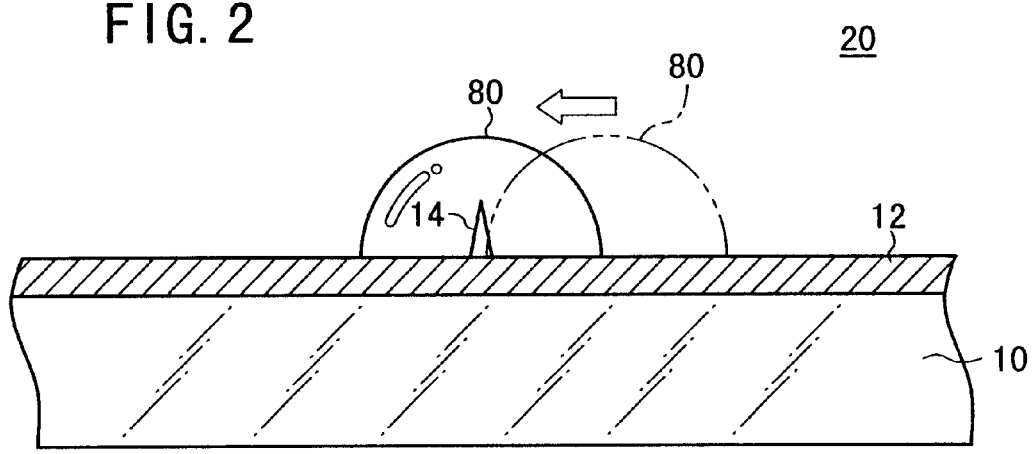
FIG. 2 shows a magnified sectional view illustrating an arrangement of the DNA chip according to the embodiment of the present invention.

Specifically, as shown in FIG. 2, a poly-L-lysine layer 12 having a hydrophilic property is formed on the surface of the base plate 10. Projections 14 are formed at respective central portions of positions on which the minute spots 80 are to be formed respectively. The projections 14 function as the positional deviation-correcting means.

That is, as shown in FIG. 2, upon the formation of the minute spot 80 by supplying the sample solution onto the base plate 10, when a part of the minute spot 80 contacts with the projection (see two-dot chain line), then the minute spot 80 is moved in accordance with the surface tension of the minute spot 80, and the central position of the minute spot 80 approximately coincides with the projection 14.

As described above, in the case of the DNA chip 20 according to the embodiment of the present invention, even when the minute spot 80 is dripped while being deviated from the prescribed position, then the minute spot 80 is moved by the projection 14 formed on the base plate 10, and the positional deviation is corrected.

Figure 3:
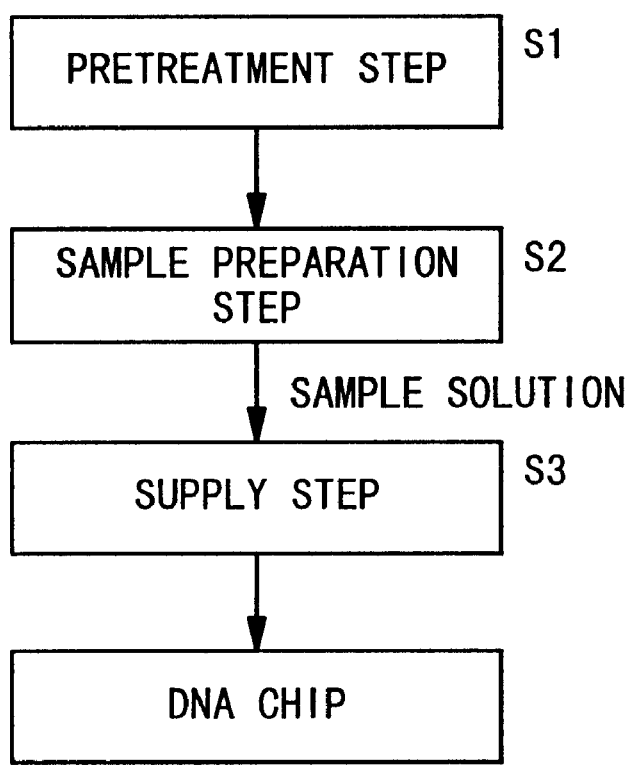
FIG. 3 shows a block diagram illustrating the steps of the method for producing the DNA chip according to the embodiment of the present invention.

When the DNA chip 20 is produced by forming the minute spot 80 by supplying the sample solution onto the base plate 10, for example, production steps as shown in FIG. 3 are carried out.

That is, the DNA chip 20 is produced by executing the pretreatment step S1 for forming the poly-L-lysine layer 12 (see FIG. 2) on the surface of the base plate 10, the sample preparation step S2 for preparing the sample solution containing a DNA fragment, and the supply step S3 for supplying the obtained sample solution onto the base plate 10.

Figure 4:
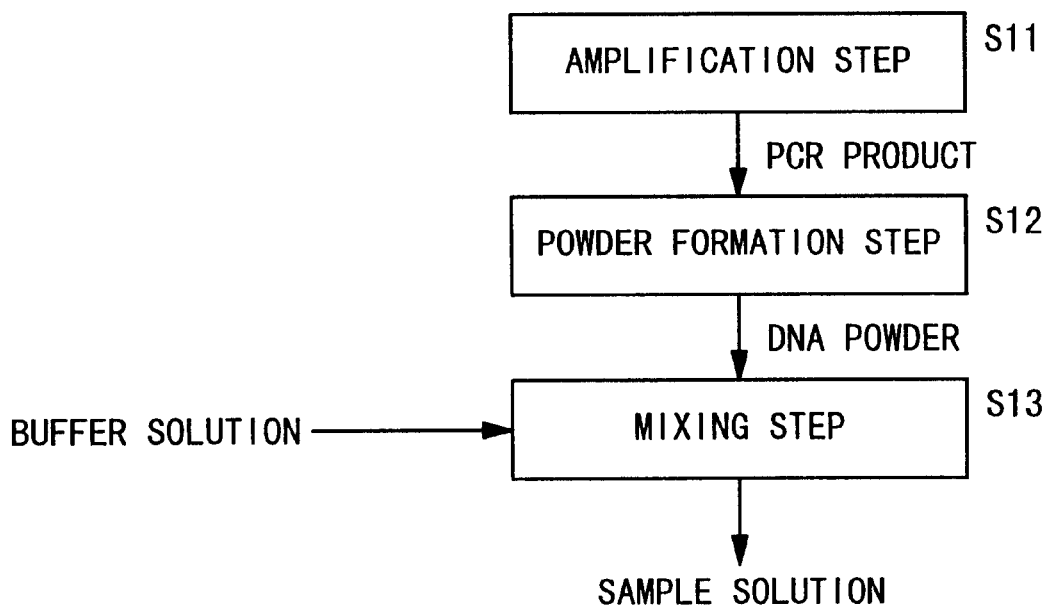
FIG. 4 shows a block diagram illustrating details of the step of preparing a sample.

As shown in FIG. 4, the sample preparation step S2 includes the amplification step S11 for PCR-amplifying the DNA fragment to prepare a PCR product, the powder formation step S12 for drying the obtained PCR product to give DNA powder, and the mixing step S13 for dissolving the obtained DNA powder in a buffer solution.

The steps will be specifically explained. In the pretreatment step S1, at first, the base plate 10 is immersed in an alkaline solution, followed by being gently shaken for at least 2 hours at room temperature. The alkaline solution is a solution obtained, for example, by dissolving NaOH in distilled water and adding ethanol thereto, followed by being agitated until the solution is completely transparent.

After that, the base plate 10 is taken out, and it is transferred into distilled water, followed by being rinsed to remove the alkaline solution. Subsequently, the base plate 10 is immersed in a poly-L-lysine solution prepared by adding poly-L-lysine to distilled water, followed by being left to stand for 1 hour.

After that, the base plate 10 is taken out, and it is applied to a centrifugal machine to perform centrifugation so that any excessive poly-L-lysine solution is removed. Subsequently, the base plate 10 is dried at 40° C. for about 5 minutes to obtain the base plate 10 comprising the poly-L-lysine layer 12 formed on the surface.

Subsequently, in the sample preparation step S2, at first, 3 M sodium acetate and isopropanol are added to the PCR product amplified with a known PCR equipment (amplification step S11), followed by being left to stand for several hours. After that, the PCR product solution is centrifuged with a centrifugal machine to precipitate the DNA fragment.

The precipitated DNA fragment is rinsed with ethanol, and it is centrifuged, followed by being dried to produce the DNA powder (powder formation step S12). A ×1 TE buffer is added to the obtained DNA powder, followed by being left to stand for several hours to completely dissolve the DNA powder (mixing step S13). Thus, the sample solution is prepared. At this stage, the concentration of the sample solution is 1 to 10 $\mu g/\mu l$. An immobilizing solution may be supplied thereafter from a sample-pouring port 52 into a cavity 56.

In the embodiment of the present invention, the obtained sample solution is supplied onto the base plate 10 to produce the DNA chip 20 (supply step S3). The immobilizing solution may be mixed with the sample solution obtained by carrying out the sample preparation step S2, or the sample solution may be diluted. In this procedure, an aqueous solution containing water and NaCl or an aqueous solution containing polymer can be used as a dilution solution.

When the DNA chip 20 is produced in this embodiment, for example, a dispenser 30 shown in FIGS. 5A to 7 is effectively used.

Figure 5A:
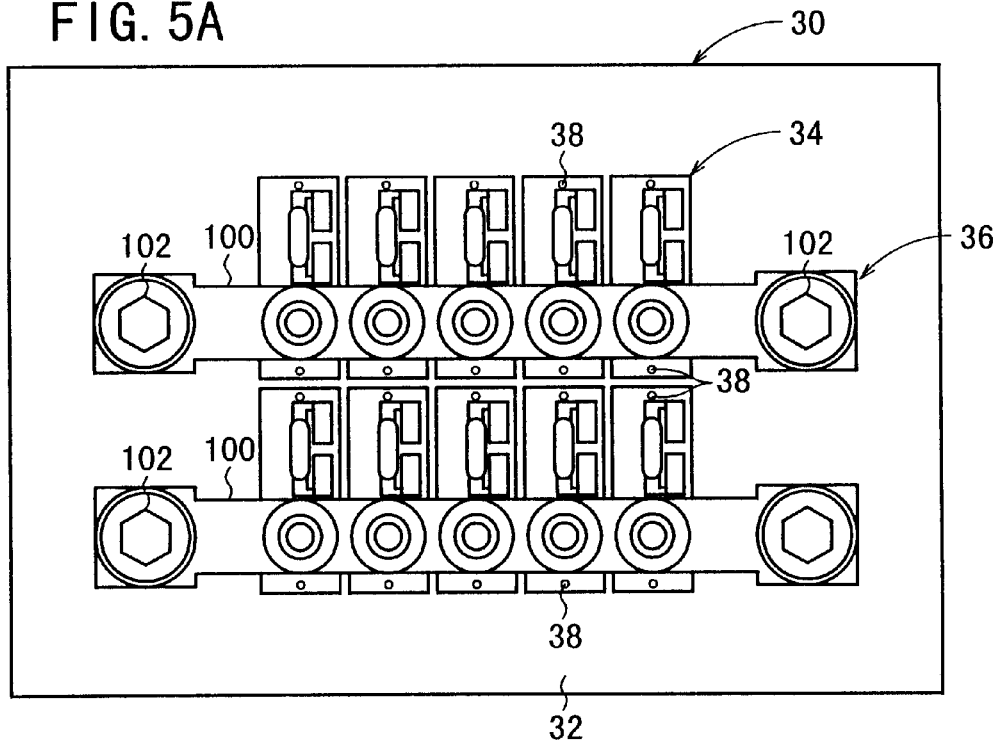
FIG. 5A shows a plan view illustrating an arrangement of a dispenser to be used for the method for producing the DNA chip according to a first embodiment.
Figure 5B:
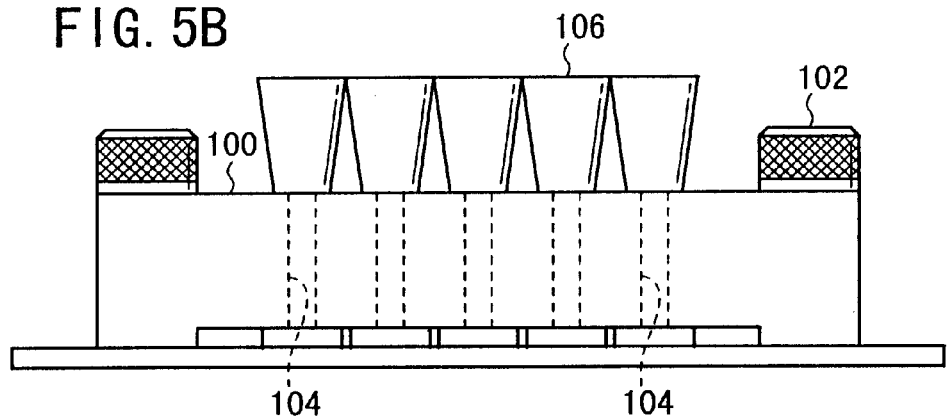
FIG. 5B shows a front view thereof.

As shown in FIGS. 5A and 5B, the dispenser 30 includes, for example, ten micropipettes 34 which are arranged in five rows and two columns on the upper surface of a fixation plate 32 having a rectangular configuration. A group of the micropipettes 34, which are aligned in the direction of the respective columns, are fixed on the fixation plate 32 by the aid of a fixing jig 36 respectively.

Figure 5C:
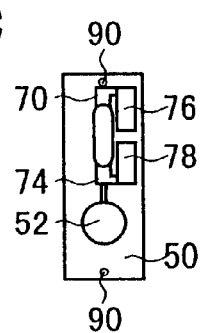
FIG. 5C shows a magnified plan view illustrating one micropipette for constructing the dispenser.
Figure 6:
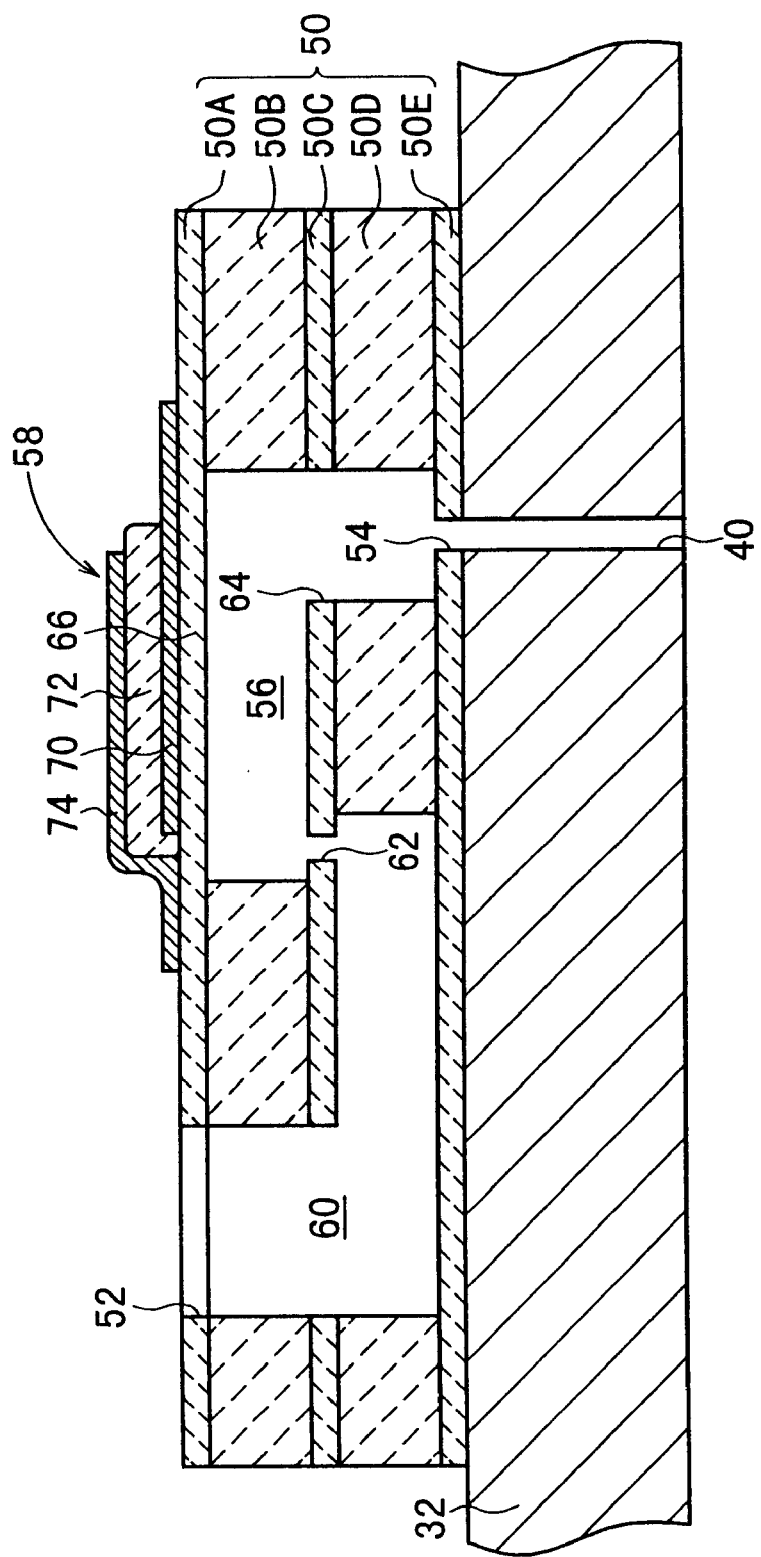
FIG. 6 shows a longitudinal sectional view illustrating an arrangement of the micropipette.

As shown in FIGS. 5C and 6, the micropipette 34 comprises a sample-pouring port 52 which is formed at the upper surface of a substrate 50 having a substantially rectangular parallelepiped-shaped configuration, a sample discharge port 54 which is formed at the lower surface of the substrate 50, a cavity 56 which is formed at the inside between the sample-pouring port 52 and the sample discharge port 54, and an actuator section 58 which is used to vibrate the substrate 50 or change the volume of the cavity 56.

Therefore, as shown in FIG. 6, through-holes 40 are provided through the fixation plate 32 at portions corresponding to the sample discharge ports 54 of the micropipettes 34 respectively. Accordingly, the sample solution, which is discharged from the sample discharge port 54 of the micropipette 34, is supplied through the through-hole 40, for example, to the base plate 20 which is fixed under the fixation plate 32.

An introducing bore 60 having a substantially L-shaped configuration with a wide opening width is formed over a region ranging from the sample-pouring port 52 to the inside of the substrate 50 in the micropipette 34. A first communication hole 62 having a small diameter is formed between the introducing bore 60 and the cavity 56. The sample solution, which is poured from the sample-pouring port 52, is introduced into the cavity 56 through the introducing bore 60 and the first communication hole 62.

A second communication hole 64, which communicates with the sample discharge port 54 and which has a diameter larger than that of the first communication hole 62, is formed at a position different from that of the first communication hole 62, of the cavity 56. In the embodiment of the present invention, the first communication hole 62 is formed at the portion of the lower surface of the cavity 56. The position of the first communication hole 62 is deviated toward the sample-pouring port 52. The second communication hole 64 is formed at the position of the lower surface of the cavity 56 as well corresponding to the sample discharge port 54.

Further, in this embodiment, the portion of the substrate 50, with which the upper surface of the cavity 56 makes contact, is thin-walled to give a structure which tends to undergo the vibration with respect to the external stress so that the portion functions as a vibrating section 66. The actuator section 58 is formed on the upper surface of the vibrating section 66.

The substrate 50 is constructed by laminating a plurality of green sheets made of zirconia ceramics (first thin plate layer 50A, first spacer layer 50B, second thin plate layer 50C, second spacer layer 50D, and third thin plate layer 50E), followed by sintering into one unit.

That is, the substrate 50 is constructed by laminating the thin-walled first thin plate layer 50A which is formed with a window for constructing the sample-pouring port 52 and which constitutes a part of the vibrating section 66, the thick-walled first spacer layer 50B which is formed with a part of the introducing bore 60 and a plurality of windows for constructing the cavity 56 respectively, the thin-walled second thin plate layer 50C which is formed with a part of the introducing bore 60 and a plurality of windows for constructing a part of the second communication hole 64 and the first communication hole 62 respectively, the thick-walled second spacer layer 50D which is formed with a plurality of windows for constructing a part of the introducing bore 60 and a part of the second communication hole 64 respectively, and the thin-walled third thin plate layer 50E which is formed with a window for constructing the sample discharge port 54, followed by sintering into one unit.

The actuator section 58 is constructed to have the vibrating section 66 described above as well as a lower electrode 70 which is directly formed on the vibrating section 66, a piezoelectric layer 72 which is composed of, for example, a piezoelectric/electrostrictive layer or an anti-ferroelectric layer formed on the lower electrode 70, and an upper electrode 74 which is formed on the upper surface of the piezoelectric layer 72.

As shown in FIG. 5C, the lower electrode 70 and the upper electrode 74 are electrically connected to an unillustrated driving circuit via a plurality of pads 76, 78 which are formed on the upper surface of the substrate 50 respectively.

The micropipette 34 constructed as described above is operated as follows. That is, when an electric field is generated between the upper electrode 74 and the lower electrode 70, then the piezoelectric layer 72 is deformed, and the vibrating section 66 is deformed in accordance therewith. Accordingly, the volume of the cavity (pressurizing chamber) 56 contacting with the vibrating section 66 is decreased.

When the volume of the cavity 56 is decreased, the sample solution charged in the cavity 56 is discharged at a predetermined speed from the sample discharge port 54 which communicates with the cavity 56. As shown in FIG. 1, it is possible to prepare the DNA chip 20 in which the sample solutions discharged from the micropipettes 34 are aligned and fixed as the minute spots 80 on the base plate 10 such as a microscopic slide glass.

In this embodiment, the arrangement pitch of the sample discharge ports 54 of the dispenser 30 is larger then the arrangement pitch of the minute spots 80 to be formed on the base plate 10. Therefore, the sample solution is supplied while deviating the supply position for the dispenser 30.

During this process, even when any dispersion arises in the deviation width for the dispenser 30 or the arrangement pitch of the sample discharge ports 54, then the minute spots 80, which are formed by supplying the sample solutions, are moved to the prescribed positions respectively by the aid of the projections 14 formed on the base plate 10, and the positional deviation is corrected. Accordingly, in this embodiment, the arrangement state of the large number of minute spots 80 to be formed on the base plate 10 can be in the state which conforms to the prescribed arrangement pitch.

Further, it is also preferable that the movement of the minute spot 80 is facilitated by adding water to the base plate 10 so that the minute spot 80 is moved toward the projection 14. It is also possible to expect such an effect that the cross-sectional configuration of the minute spot 80 gathered to the projection 14 can be corrected to give a hemispherical configuration, which is preferred.

An apparatus structure based on the so-called ink-jet system may be adopted as the structure in which the volume of the cavity 56 is decreased in accordance with the driving of the actuator section 58 (see Japanese Laid-Open Patent Publication No. 6-40030).

It is preferable that the cavity (pressurizing chamber) 56 is formed to have such a flow passage dimension that the sample solution containing DNA fragments or the like is moved in a laminar flow.

Figure 7:
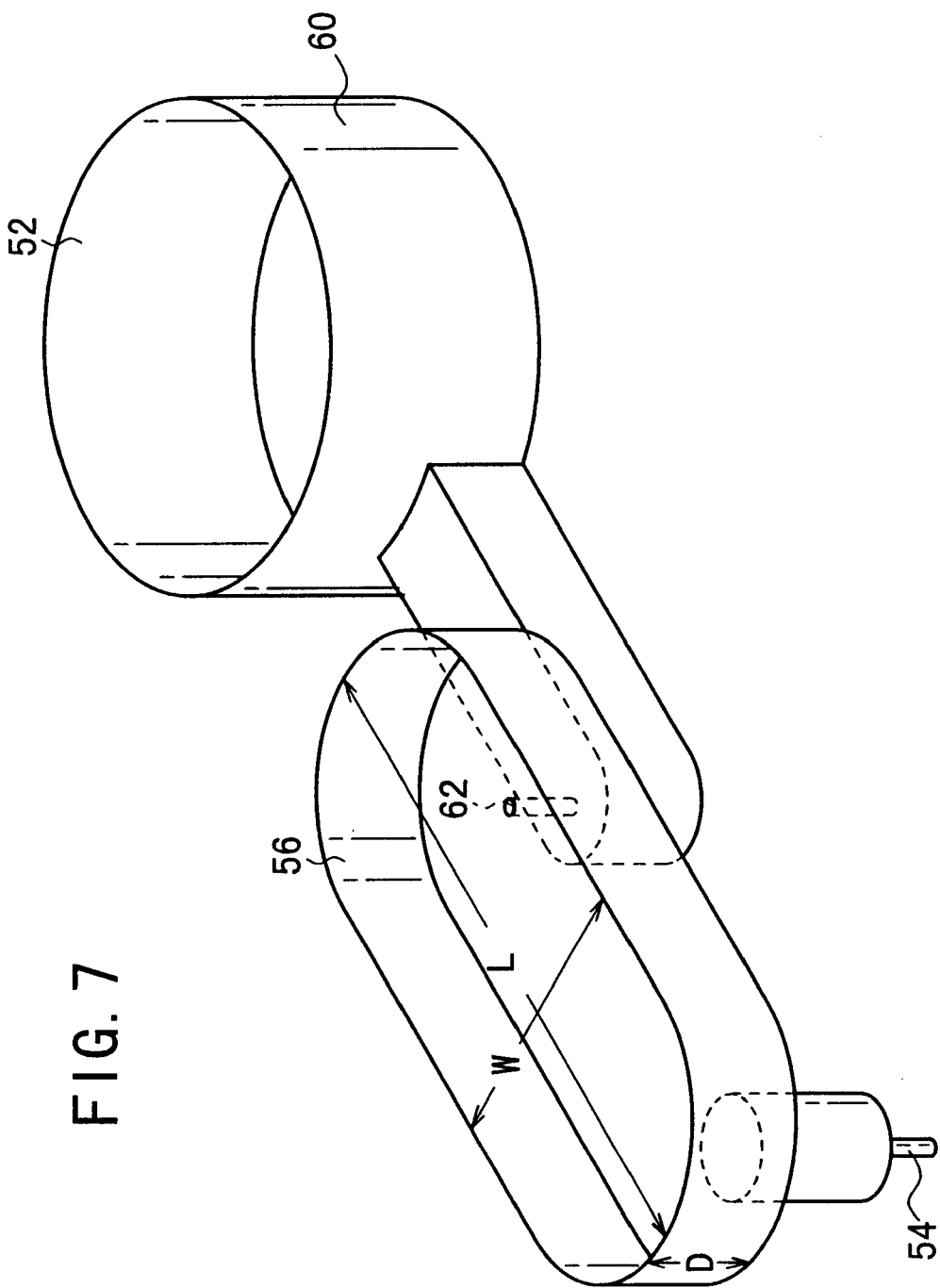
FIG. 7 shows a perspective view illustrating a shape of a flow passage including a cavity formed in a substrate of the micropipette.

That is, the dimension of the cavity 56 differs depending on the type of the sample, the size of liquid droplets to be prepared, and the density of formation. However, for example, when a sample, which is obtained by dispersing DNA fragments of base pairs of about 1 to 10,000 in a buffer solution (TE buffer) at a concentration of 1 $\mu$g/$\mu$l, is dripped at a pitch of several hundreds $\mu$m to give a liquid droplet diameter of several hundreds $\mu$m$\phi$, then it is preferable that the cavity length (L) is 1 to 5 mm, the cavity width (W) is 0.1 to 1 mm, and the cavity depth (D) is 0.1 to 0.5 mm as shown in FIG. 7. It is preferable that the inner wall of the cavity 56 is smooth without involving any projection to disturb the flow. It is more preferable that the material of the cavity 56 is made of ceramics which has good affinity with respect to the sample solution.

When the shape as described above is adopted, the cavity 56 can be used as a part of the flow passage ranging from the sample-pouring port 52 to the sample discharge port 54. The sample can be introduced to the sample discharge port 54 without disturbing the flow of the sample solution which is moved from the sample-pouring port 52 via the introducing bore 60 and the first communication hole 62 to the inside of the cavity 56.

As shown in FIG. 5A, a plurality of pins 38 for positioning and fixing the micropipettes 34 are provided on the upper surface of the fixation plate 32. When the micropipette 34 is fixed on the fixation plate 32, the micropipette 34 is placed on the fixation plate 32 while inserting the pins 38 of the fixation plate 32 into positioning holes 90 (see FIG. 5C) provided at the both sides of the substrate 50 of the micropipette 34. Thus, a plurality of micropipettes 34 are automatically aligned and positioned with a predetermined array arrangement.

Each of the fixing jigs 36 has a holder plate 100 for pressing the plurality of micropipettes 34 against the fixation plate 32. Insertion holes for inserting screws 102 thereinto are formed through both end portions of the holder plate 100. When the screws 102 are inserted into the insertion holes, and they are screwed into the fixation plate 32, then the plurality of micropipettes 34 can be pressed against the fixation plate 32 by the aid of the holder plate 100 at once. One unit is constructed by the plurality of micropipettes 34 which are pressed by one holder plate 100. The example shown in FIG. 5A is illustrative of the case in which one unit is constructed by the five micropipettes 34 which are arranged in the direction of the column.

The holder plate 100 is formed with introducing holes 104 (see FIG. 5B) which are used to supply the sample solutions to the portions corresponding to the sample-pouring ports 52 of the respective micropipettes 34 respectively when the plurality of micropipettes 34 are pressed. Tubes 106 for introducing the sample solution to the introducing holes 104 respectively are held at upper end portions of the respective introducing holes 104.

Considering the realization of the efficient wiring operation, it is preferable that the width of the holder plate 100 resides in such a dimension that the pads 76, 78 connected to the respective electrodes 70, 74 of the actuator section 58 are faced upwardly when the plurality of micropipettes 34 are pressed against the fixation plate 32.

As described above, the dispenser 30 is constructed such that the plurality of micropipettes 34 each having the sample-pouring port 52 and the sample discharge port 54 are provided in an upstanding manner with the respective sample discharge ports 54 directed downwardly.

That is, the respective micropipettes 34 are aligned and arranged such that the respective sample-pouring ports 52 are disposed on the upper side, the sample discharge ports 54 are disposed on the lower side, and the respective sample discharge ports 54 are aligned two-dimensionally. Sample solutions of mutually different types are discharged from the sample discharge ports 54 respectively.

Figure 8:
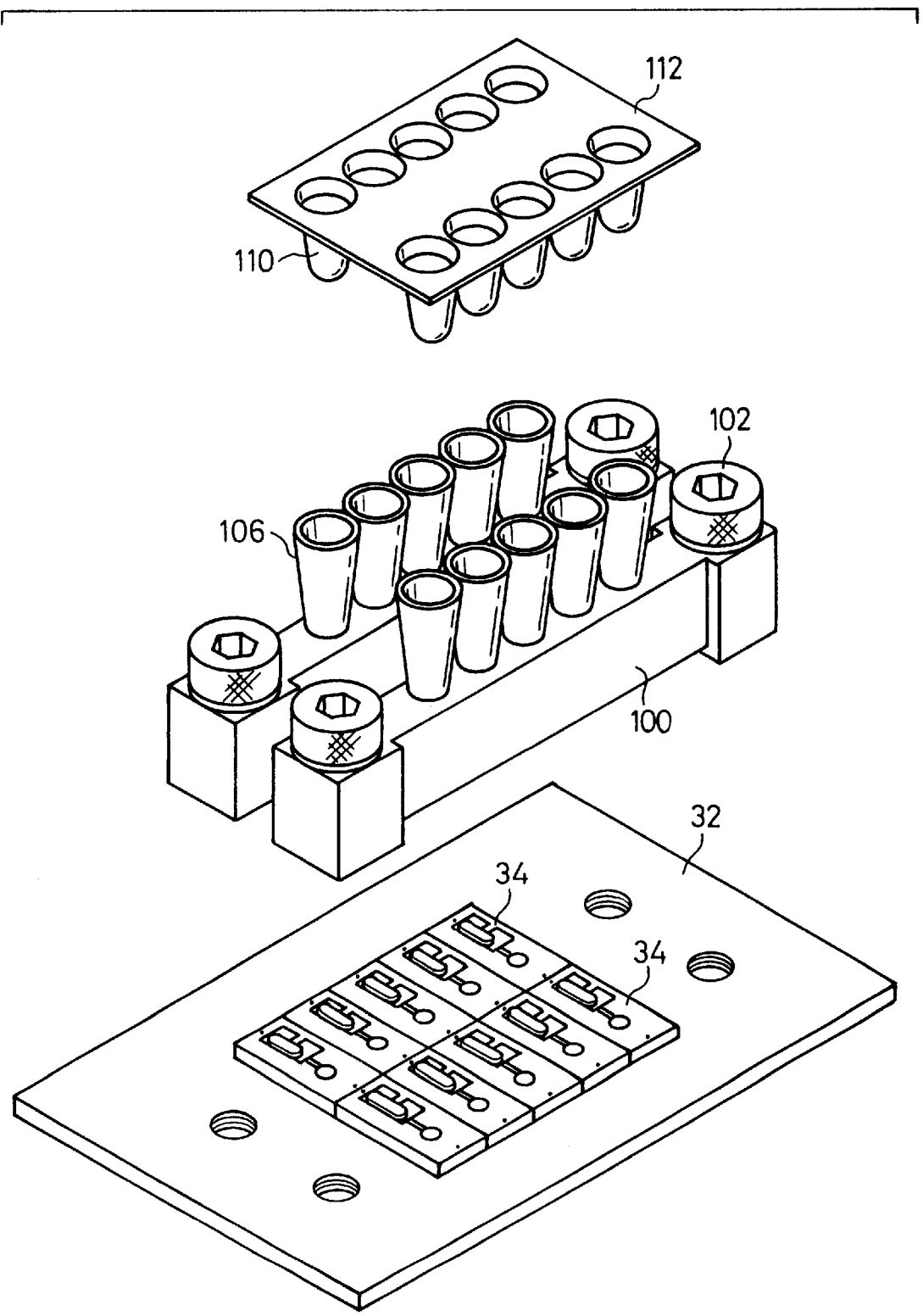
FIG. 8 shows an exploded perspective view illustrating the dispenser together with a cartridge.

When the dispenser 30 constructed as described above is used, several methods are available to supply the sample solutions of mutually different types corresponding to the respective sample-pouring ports 52. That is, as shown in FIG. 8, for example, a method is available, which is based on the used of a cartridge 112 arranged with a large number of recesses (storage sections) 110 each having a substantially V-shaped cross section. For this method, for example, the following procedure is available. That is, the mutually different sample solutions are poured into the respective recesses 110 of the cartridge 112. The cartridge 112 is attached so that the respective recesses 110 correspond to the tubes 106 respectively. The bottoms of the respective recesses 110 are opened with needles or the like. Accordingly, the sample solutions having been charged in the respective recesses 110 are supplied via the tubes 106 to the respective micropipettes 34.

When the tubes 106 are not used, for example, the following method is available. That is, the cartridge 112 is attached so that the respective recesses 110 correspond to the respective introducing holes 104 of the fixing jig 36. The bottoms of the respective recesses 110 are opened with needles or the like. Accordingly, the sample solutions having been charged in the respective recesses 110 are supplied via the introducing holes 104 to the respective micropipettes 34. Alternatively, needles or the like may be formed in the vicinity of the respective introducing holes 104 of the fixing jig 36 so that the respective recesses 110 may be opened simultaneously with the attachment of the cartridge 112 to the fixing jig 36.

Alternatively, it is also preferable to add a mechanism for feeding the gas or the like under the pressure after the opening to forcibly extrude the sample solutions. It is desirable to provide a mechanism for washing the space ranging from the sample-pouring port 52 to the sample discharge port 54 formed at the inside of the substrate 50 of each of the micropipettes 34, for example, in order that several thousands to several tens thousands types or many kinds of DNA fragments are discharged as the minute spots 80 with good purity without involving any contamination.

In the example shown in FIG. 5A, the both ends of the holder plate 100 are tightened to the fixation plate 20 by the aid of the screws 102. However, the holder plate 100 may be fixed in accordance with other methods based on the mechanical procedure by using screws and springs, as well as based on an adhesive or the like.

As described above, the substrate 50 for constructing the micropipette 34 is formed of ceramics, for which it is possible to use, for example, fully stabilized zirconia, partially stabilized zirconia, alumina, magnesia, and silicon nitride.

Among them, the fully stabilized/partially stabilized zirconia is used most preferably, because the mechanical strength is large even in the case of the thin plate, the toughness is high, and the reactivity with the piezoelectric layer 72 and the electrode material is small.

When the fully stabilized/partially stabilized zirconia is used as the material, for example, for the substrate 50, it is preferable that the portion (vibrating section 66), on which the actuator section 58 is formed, contains an additive such as alumina and titania.

Those usable as the piezoelectric ceramic for the piezoelectric layer 72 for constructing the actuator section 58 include, for example, lead zirconate, lead titanate, lead magnesium niobate, lead magnesium tantalate, lead nickel niobate, lead zinc niobate, lead manganese niobate, lead antimony stannate, lead manganese tungstate, lead cobalt niobate, and barium titanate, as well as composite ceramics containing components obtained by combining any of them. However, in the embodiment of the present invention, a material containing a major component composed of lead zirconate, lead titanate, and lead magnesium niobate is preferably used, because of the following reason.

That is, such a material has a high electromechanical coupling constant and a high piezoelectric constant. Additionally, such a material has small reactivity with the substrate material during the sintering of the piezoelectric layer 72, making it possible to stably form the product having a predetermined composition.

Further, in the embodiment of the present invention, it is also preferable to use ceramics obtained by appropriately adding, to the piezoelectric ceramics described above, for example, oxides of lanthanum, calcium, strontium, molybdenum, tungsten, barium, niobium, zinc, nickel, manganese, cerium, cadmium, chromium, cobalt, antimony, iron, yttrium, tantalum, lithium, bismuth, and stannum, or a combination of any of them, or other compounds.

For example, it is also preferable to use ceramics containing a major component composed of lead zirconate, lead titanate, and lead magnesium niobate, and further containing lanthanum and/or strontium.

On the other hand, it is preferable that the upper electrode 74 and the lower electrode 70 of the actuator section 58 are made of metal which is solid at room temperature and which is conductive. For example, it is possible to use metal simple substance of, for example, aluminum, titanium, chromium, iron, cobalt, nickel, copper, zinc, niobium, molybdenum, ruthenium, palladium, rhodium, silver, stannum, tantalum, tungsten, iridium, platinum, gold, and lead, or alloy obtained by combining any of them. It is also preferable to use a cermet material obtained by dispersing, in the metal described above, the same material as that of the piezoelectric layer 72 or the substrate 50.

Next, explanation will be made with reference to FIGS. 9 and 10 for several methods for producing the DNA chip 20 by using the dispenser 30.

Figure 9:
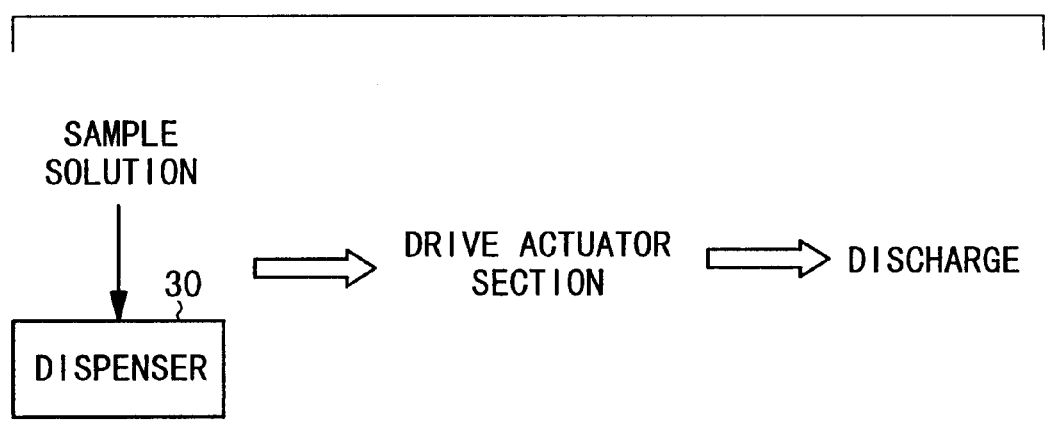
FIG. 9 illustrates a first method in which the DNA chip is produced by using the dispenser.
Figure 10:
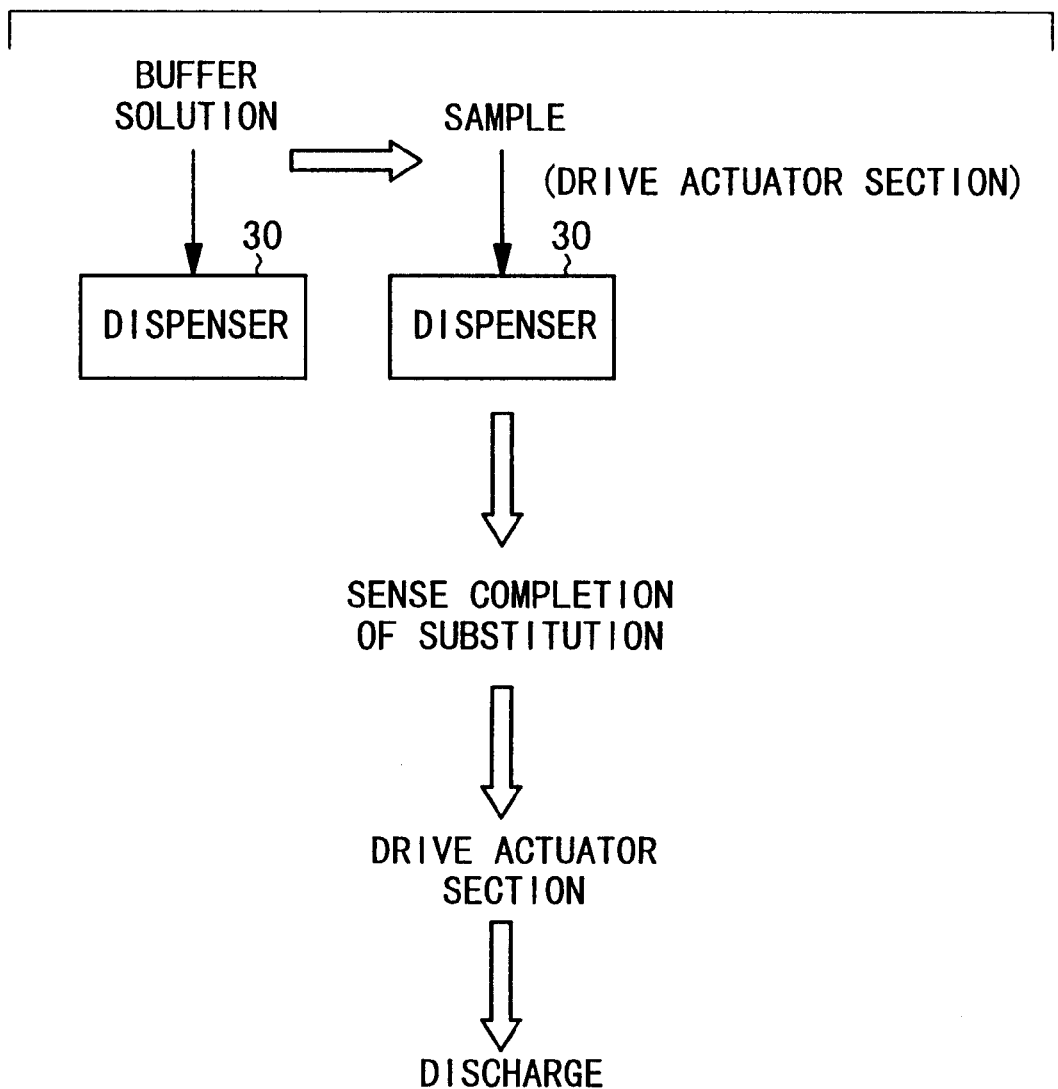
FIG. 10 illustrates a second method in which the DNA chip is produced by using the dispenser.

At first, a first method is shown in FIG. 9. That is, mutually different types of sample solutions are charged from the respective tubes 106 via the introducing holes 104 of the fixing jig 36 into the cavities 56 of the respective micropipettes 34 respectively. Subsequently, the respective actuator sections 58 are driven to discharge the sample solutions from the sample discharge ports 54 of the respective micropipettes 34. As for the method for charging the solution into the cavity 56, the solution may be poured in accordance with the capillary force of the solution introduced from the sample-pouring port 52. However, it is reliable to adopt a method in which the solution is charged by means of vacuum aspiration through the sample discharge port 54.

As for the voltage waveform to be applied to the respective electrodes 70, 74 of the actuator section 58, when the actuator section 58 is subjected to the ON operation to decrease the volume of the cavity 56, a pulsed voltage is applied to the respective electrodes 70, 74. In this case, the deformation of the vibrating section 66 is increased by increasing the amplitude of the pulse, and the discharge amount of the sample solution is also increased in accordance therewith. When a plurality of pulses are applied for a certain period, a large number of sample solutions each having a small amount can be discharged by shortening the pulse cycle and decreasing the amplitude of each pulse.

During this process, when the supply position is appropriately changed, the droplets of the supplied sample solution are combined (integrated) on the base plate 10 to form the sample solution having one spot diameter. However, it is possible to realize a uniform spot diameter formed on the base plate 10 by controlling the number of supply operations, the supply position, and the amount of one time supply, depending on the type of the sample solution to be supplied.

Next, explanation will be made for a second method based on the use of the dispenser 30. The second method is shown in FIG. 10. That is, a substitution solution such as a buffer solution, an aqueous solution containing NaCl, and an aqueous solution containing polymer is charged into the cavity 56 of each of the micropipettes 34 from each of the tubes 106 via the introducing hole 104 of the fixing jig 36 respectively. Subsequently, the sample is poured into the cavity 56 from the sample-pouring port 52 while effecting the laminar flow substitution to wait for the completion of the substitution thereafter. After that, the actuator section 58 is driven to discharge and supply the sample solution onto the base plate 10.

It is preferable that the completion of the laminar flow substitution of the sample in the cavity 56 is recognized by sensing the change of the fluid characteristic in the cavity 56.

It is preferable that the substitution between the substitution solution and the sample solution in the cavity 56 is performed in a form of the laminar flow. However, when the type of the sample is changed, or when the movement speed of the liquid is extremely fast, then it is not necessarily indispensable to use the laminar flow at portions of the cavity 56 in the vicinity of the first communication hole 62. In this case, the purge amount of the sample solution is increased due to the mixing of the sample and the substitution solution. However, it is possible to suppress the increase in the purge amount to be minimum by judging the completion of the substitution by sensing the change of the fluid characteristic in the cavity 56.

In the present invention, the change of the fluid characteristic in the cavity 56 is recognized by applying a voltage in such a degree as to excite the vibration in the actuator section 58, and detecting the change of the electric constant caused by the vibration. Such a procedure for sensing the change of the fluid characteristic is disclosed, for example, in Japanese Laid-Open Patent Publication No. 8-201265.

Specifically, the electric connection from a power source for driving the discharge is separated from the actuator section 58 at a predetermined interval by using a relay. Simultaneously, a means for measuring the resonance frequency is connected by using the relay. At this point of time, the impedance or the resonance characteristic such as the resonance frequency or the attenuation factor is electrically measured.

Accordingly, it is possible to recognize, for example, whether or not the viscosity and the specific gravity of the liquid are those of the objective sample (liquid containing the DNA fragment or the like). That is, as for each of the micropipettes 34, the micropipette 34 itself functions as a sensor. Therefore, it is also possible to simplify the structure of the micropipette 34.

The actuator section 58 is driven under a driving condition corresponding to the amount of liquid droplets suitable for the required spot diameter, and the sample solution is repeatedly supplied. Accordingly, the DNA chip 20 is produced. Usually, when one minute spot 80 is formed, one to several hundreds of droplet or droplets are discharged from the micropipette 34.

When the amount of the sample in the sample-pouring port 52 is decreased, the discharge is continued by adding the buffer solution so that no bubble enters the inside of the flow passage. Accordingly, all of the sample solution can be used without allowing the sample solution to remain in the micropipette 34. The completion of the substitution from the sample to the substitution solution (completion of the sample discharge) is confirmed by detecting the viscosity and the specific gravity of the liquid by using the actuator section 58 in the same manner as described above.

It is preferable to use the substitution solution and the sample solution such that the dissolved gas in the solution is previously removed by performing the degassing operation. When such a solution is used, if any bubble obstructs the flow passage at an intermediate portion to cause the defective charge upon the charge of the solution into the flow passage of the micropipette 34, then the inconvenience can be avoided by dissolving the bubble in the solution. Further, no bubble is generated in the fluid during the discharge, and no defective discharge is caused as well.

In the second method described above, the substitution solution such as a buffer solution, an aqueous solution containing NaCl, and an aqueous solution containing polymer is poured from the sample-pouring port 52 into the cavity 56 while discharging the sample solution, and the sample solution remaining in the cavity 56 is completely discharged to make provision for the next pouring of the sample.

When it is sensed whether or not the sample solution remains in the cavity 56 (whether or not the discharge can be effected as the sample solution), the recognition can be also made by sensing the change of the fluid characteristic in the cavity 56. In this case, a mechanism for detecting the completion of the substitution can be used to extremely decrease the purge amount of the sample which is not used and improve the efficiency of the use of the sample solution.

It is also preferable that when the sample is charged from the sample-pouring port 52 to the cavity 56, the interior of the cavity 56 is substituted with the sample from the sample-pouring port 52 while driving the actuator section 58. In this procedure, the interior of the cavity 56 can be completely substituted in a reliable manner with the inexpensive substitution solution beforehand. As a result, it is possible to completely avoid the occurrence of any defective discharge, and it is possible to efficiently discharge the expensive sample.

Further, the following procedure may be adopted. That is, the substitution solution such as a buffer solution, an aqueous solution containing NaCl, and an aqueous solution containing polymer is charged into the cavity 56. The amount of the substitution solution existing in the cavity 56 and in the sample-pouring port 52 is adjusted to be a predetermined amount. Subsequently, a predetermined amount of the sample solution is poured from the sample-pouring port 52, and then the actuator section 58 is driven in an amount corresponding to a predetermined number of pulses to discharge the amount of the substitution solution existing in the cavity 56 and in the sample-pouring port 52.

By doing so, the amount of the substitution solution existing in the cavity 56 and in the sample-pouring port 52 is correctly discharged, and it is possible to complete the charge of the sample solution without any loss.

As described above, in the DNA chip 20 according to the embodiment of the present invention, the projection 14, which serves as the positional deviation-correcting means for automatically correcting the positional deviation of the minute spot 80, is provided on the base plate 10. Therefore, when the sample solution is supplied onto the base plate 10, even if the supply position is deviated from the prescribed position, then the minute spot 80 to be formed by supplying the sample solution is moved to the prescribed position by the aid of the projection 14, and the positional deviation is corrected.

As described above, in the DNA chip 20 and the method for producing the same according to the embodiment of the present invention, even when any dispersion occurs in the deviation width of the dispenser 30 or the arrangement pitch of the sample discharge ports 54, the arrangement state of the large number of minute spots 80 formed on the base plate 10 can be the state which conforms to the prescribed arrangement pitch. Thus, it is possible to improve the quality of the DNA chip 20 and improve the yield.

Next, explanation will be made with reference to FIGS. 11 to 19B for modified embodiments of the positional deviation-correcting means provided for the base plate 10.

Figure 11:
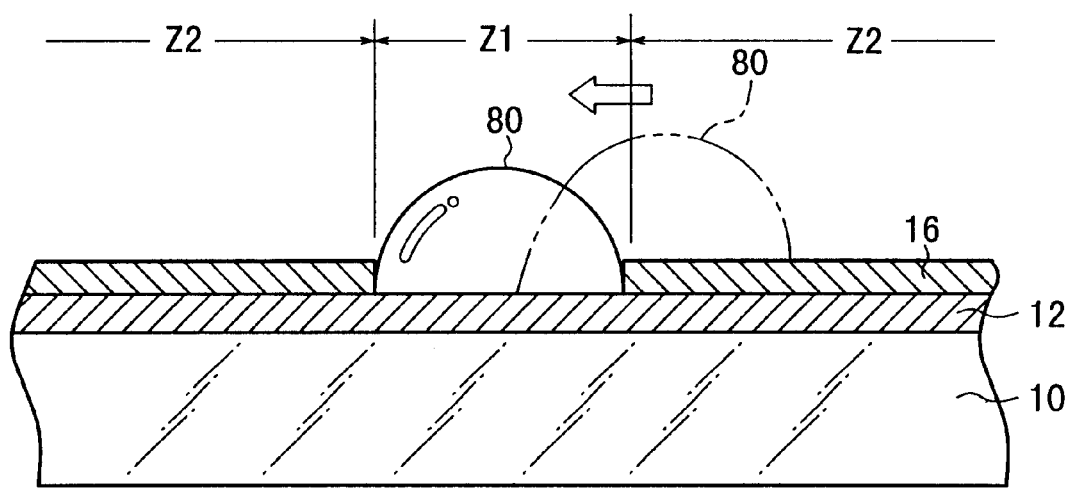
FIG. 11 shows a sectional view illustrating a positional deviation-correcting means according to a first modified embodiment.

As shown in FIG. 11, the first modified embodiment differs in that a hydrophilic zone Z1 is formed at a position of the base plate 10 at which the minute spot 80 is to be formed, and a water-repellent zone Z2 is formed at the other portions. Specifically, this arrangement is achieved by forming a water-repellent film 16 at the portions other than the position at which the minute spot 80 is to be formed. Those usable as the water-repellent film include, for example, Si coat and fluororesin.

In this arrangement, as shown in FIG. 11, upon the formation of the minute spot 80 by supplying the sample solution onto the base plate 10, when a part of the minute spot 80 contacts with the water-repellent film 16 (see two-dot chain line), then the minute spot 80 is moved in accordance with the surface tension of the minute spot 80 and the water-repellent function of the film 16, and the center of the minute spot 80 can be positioned at the prescribed position. In this case, even when the part of the minute spot 80 contacts with the water-repellent film 16, no trace is formed after the movement of the sample solution, because the film 16 is water-repellent. The shape of the spot after the immobilization is the shape which is formed by only the hydrophilic portion. Thus, the dispersion of the shape is reduced.

Figure 12:
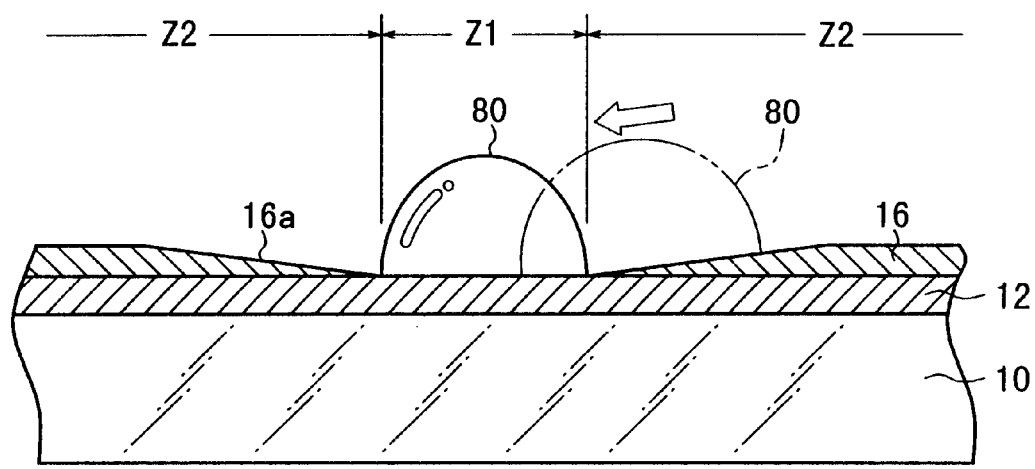
FIG. 12 shows a sectional view illustrating a positional deviation-correcting means according to a second modified embodiment.

The second modified embodiment is shown in FIG. 12. In this modified embodiment, a tapered surface 16a, which is inclined downwardly toward the hydrophilic zone Z1, is provided at only the surroundings of the hydrophilic zone Z1 of the water-repellent film 16. In this case, as shown by a dashed line, even when the minute spot 80 contacts with the water-repellent film 16, the minute spot 80 is moved to the position at which the minute spot 80 is to be formed, in accordance with the water-repellent function of the water-repellent film 16, the surface tension of the minute spot 80, and the gravity effected by the inclination of the tapered surface. Thus, the center of the minute spot 80 can be positioned at the prescribed position.

Figure 13:
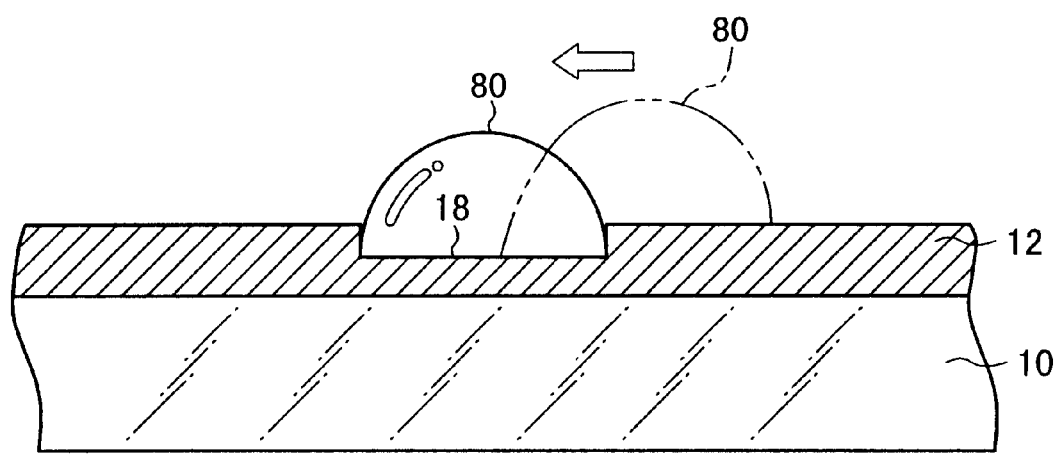
FIG. 13 shows a sectional view illustrating a positional deviation-correcting means according to a third modified embodiment.

As shown in FIG. 13, the third modified embodiment differs in that a recess 18 is formed at the position at which the minute spot 80 is to be formed on the base plate 10.

Accordingly, as shown in FIG. 13, upon the formation of the minute spot 80 by supplying the sample solution onto the base plate 10, when a part of the minute spot 80 contacts with the shoulder of the recess 18 (see two-dot chain line), then the minute spot 80 is moved in accordance with the surface tension of the minute spot 80, and the minute spot 80 can be positioned in the recess 18. In this arrangement, when the sample solution enters the recess 18, then the film thickness of the sample is made uniform, and it is possible to reduce the dispersion of the thickness of the spot. As a result, an advantage is obtained such that it is possible to suppress the deterioration of the sensitivity and the dispersion of the sensitivity when the fluorescence emitted by the spot is detected.

Figure 14:
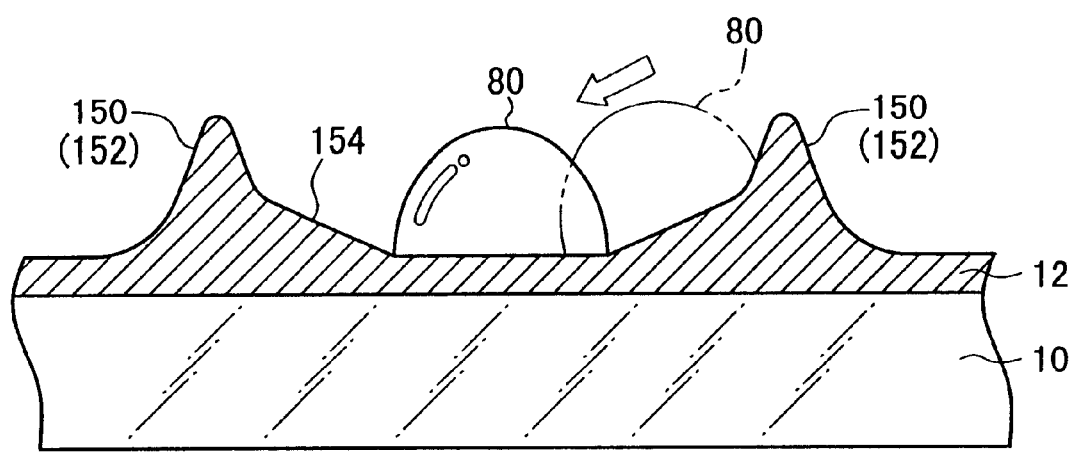
FIG. 14 shows a sectional view illustrating a positional deviation-correcting means according to a fourth modified embodiment.

The fourth modified embodiment is shown in FIG. 14. In this modified embodiment, a plurality of projections 150 are formed at the surroundings of the portion at which the minute spot 80 is formed, or an annular projection 152 is formed at the surroundings. In the case of the annular projection 152, the portion, at which the minute spot 80 is formed, is formed to have a crater-shaped configuration. In the case of the fourth modified embodiment, in addition to the effect obtained in the third modified embodiment described above, an effect is obtained such that the minute spot 80 is easily concentrated at the predetermined position (position at which the minute spot 80 is to be formed). Especially, the effect described above is further remarkable when the bottom portion of the projection 150, 152 is formed to be a gentle inclined surface 154.

The projections 150, 152 as described above can be formed on the base plate 10 by performing the spotting while appropriately adjusting, for example, the jetting pressure and the distance between the jet nozzle and the base plate 10 in the ink-jet system which is practically used for printers.

Figure 15:
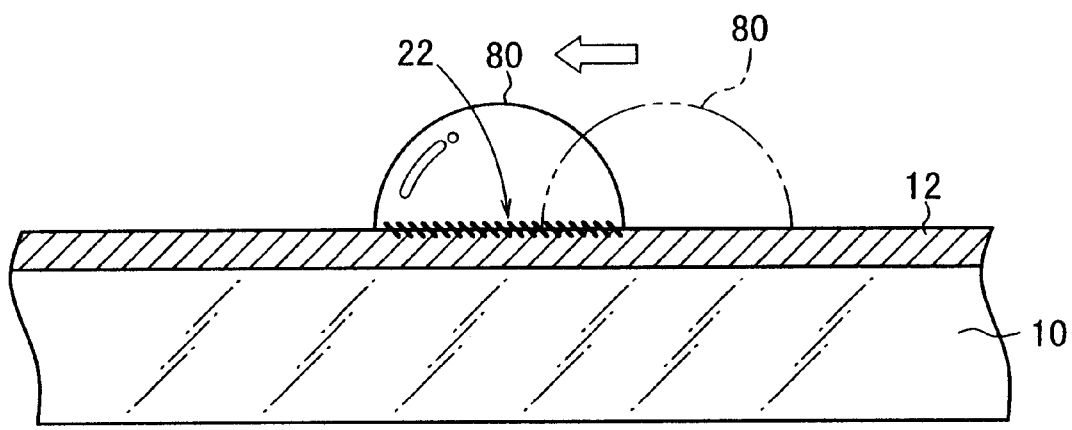
FIG. 15 shows a sectional view illustrating a positional deviation-correcting means according to a fifth modified embodiment.

As shown in FIG. 15, the fifth modified embodiment differs in that the surface state is different between the portion at which the minute spot 80 is to be formed and the other portions of the base plate 10.

Accordingly, as shown in FIG. 15, upon the formation of the minute spot 80 by supplying the sample solution onto the base plate 10, when a part of the minute spot 80 contacts with the portion other than a rough surface 22 (see two-dot chain line), then the minute spot 80 is moved in accordance with the surface tension of the minute spot 80, and the center of the minute spot 80 can be positioned at the prescribed position. In this arrangement, in the same manner as in the first modified embodiment described above, even when the part of the minute spot 80 contacts with the portion other than the rough surface 22, no trace is formed after the movement of the sample solution at the portion other than the rough surface 22. The shape of the spot after the immobilization is the shape which is formed by only the rough surface 22. Thus, the dispersion of the shape is reduced. The minute spot 80 is tightly fixed to the base plate 10 owing to the large contact area, because the contact surface is the rough surface. It is possible to reduce the flow out of the sample solution upon the immobilization after the spotting.

As for the change of the surface state, including, for example, the formation of the tapered surface 16a, the formation of the recess 18, and the formation of the rough surface 22 in the second, third, and fifth modified embodiments described above, a large amount of base plates can be processed at once, for example, by means of the blast machining, the laser machining, and the cutting machining. Such procedures are preferred, because they can be carried out inexpensively.

Figure 16:
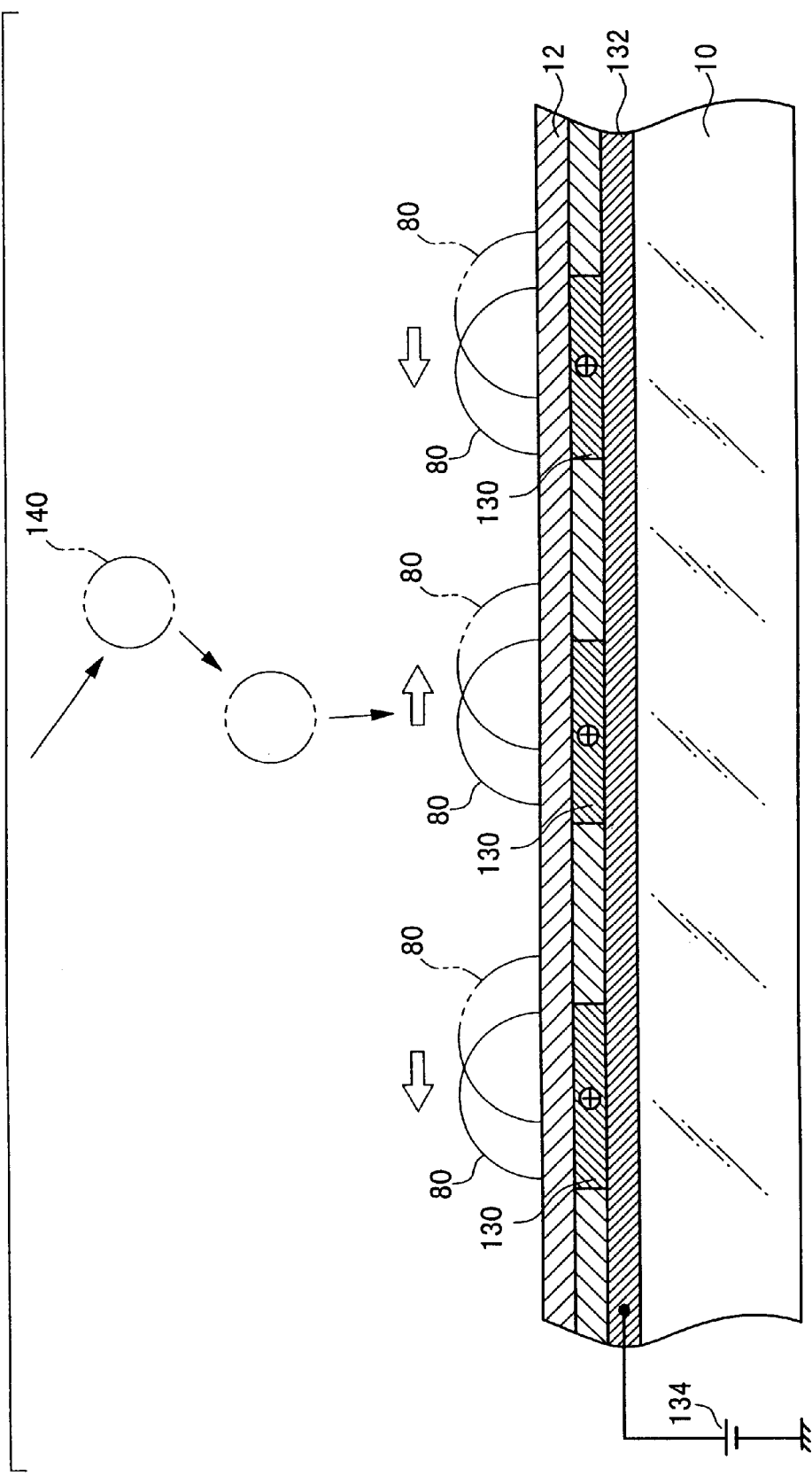
FIG. 16 shows a sectional view illustrating a positional deviation-correcting means according to a sixth modified embodiment.

In the sixth modified embodiment, the positional deviation is corrected by applying a magnetic field. Specifically, for example, as shown in FIG. 16, a large number of electrode patterns 130 based on a metal film are formed at portions corresponding to the positions at which the minute spots 80 are to be formed, in the underlying layer of a poly-L-lysine layer 12 on the base plate 10. Further, a common electrode pattern 132 based on a metal film, which is common to the pattern of the respective electrodes 130, is formed in a layer disposed thereunder.

For example, a power source 134 is connected between the common electrode pattern 132 and the ground. The respective electrode patterns 130 are charged, for example, to the plus side. In this state, when the minute spot 80 is formed by supplying the sample solution on the base plate 10, the minute spot 80 is moved onto the electrode pattern 130 in accordance with the attracting force of the electric field when a part of the minute spot 80 contacts with the portion over the electrode pattern 130 (see two-dot chain lines), because the sample solution, which constitutes the minute spot 80, is charged on the minus side. Thus, the center of the minute spot 80 is positioned at the prescribed position.

When the intensity of the electric field is increased, the liquid droplet 140, which is discharged from the sample discharge port 54 of each of the micropipettes 34, is corrected for its traveling direction in the air so that the traveling direction is directed toward the corresponding electrode pattern 130. The minute spot 80 based on the liquid droplet 140 correctly falls onto the corresponding electrode pattern 130. In this case, the liquid droplet 140 is not moved on the surface of the base plate 10. Therefore, an effect is obtained such that no trace is formed by the movement of the liquid droplet, and it is possible to obtain a stable (uniform) shape of the spot.

Figure 17:
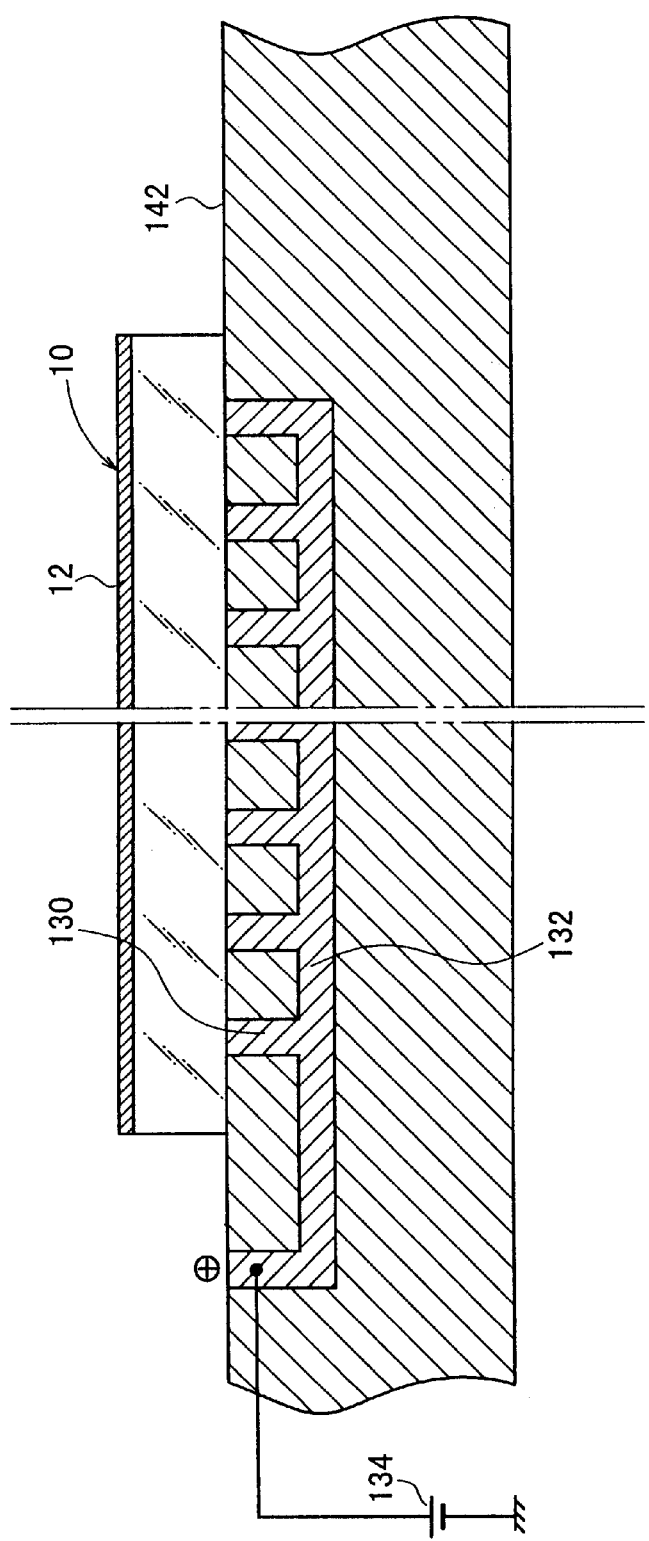
FIG. 17 shows a sectional view illustrating a positional deviation-correcting means according to a seventh modified embodiment.

As shown in FIG. 17, the seventh modified embodiment is based on substantially the same principle as that of the sixth modified embodiment described above (see FIG. 16). However, predetermined electrode patterns 130, 132 are provided on a stage 142 on which the base plate 10 is placed and fixed. In this arrangement, it is unnecessary to provide the electrode patterns 130, 132 on the base plate 10. Therefore, an advantage is obtained such that this modified embodiment can be carried out inexpensively.

The eighth modified embodiment is shown in FIG. 18. In this modified embodiment, for example, the base plate 10 is made of glass, predetermined electrode patterns 130, 132 are formed in the base plate 10, and especially the electrode pattern 130 is exposed to the surface of the base plate 10. The voltage is supplied to the electrode patterns 130, 132 by using an electrode 144 formed in a stage 142.

Figure 19A:
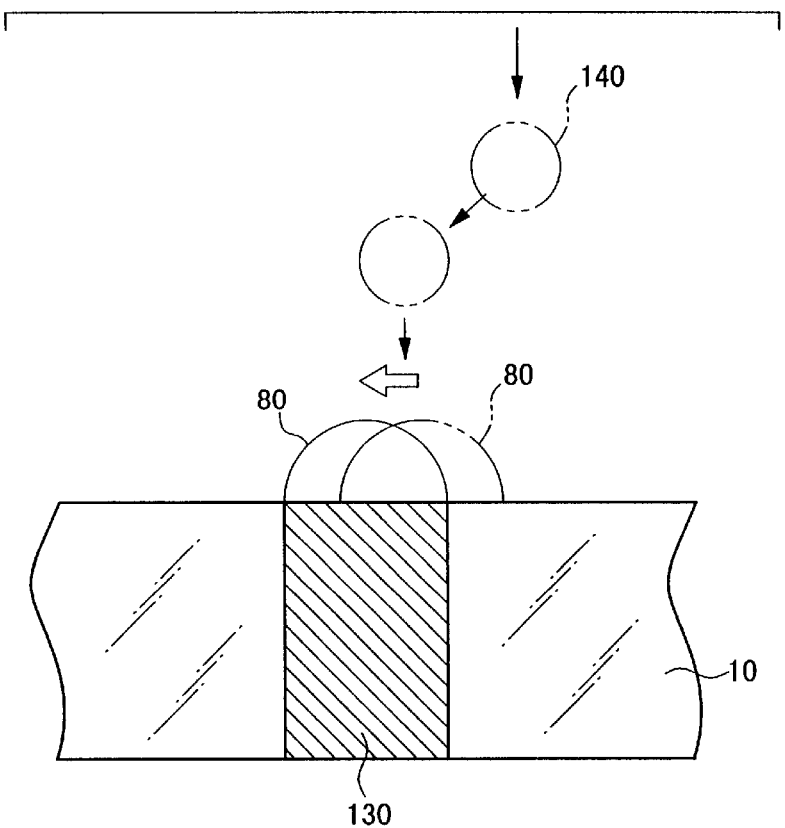
FIG. 19A illustrates the fact that an effect equivalent to that obtained in the first modified embodiment is obtained by using the positional deviation-correcting means according to the eighth modified embodiment.

In the eighth modified embodiment, the glass surface of the base plate 10 is water-repellent, and the electrode pattern 130 exposed to the glass surface is hydrophilic. Therefore, the operation is effected in the same manner as in the first modified embodiment described above. That is, for example, as shown in FIG. 19A, upon the formation of the minute spot 80 by supplying the sample solution onto the base plate 10, when a part of the minute spot 80 contacts with the water-repellent glass surface (see a two-dot chain line), the minute spot 80 is moved in accordance with the surface tension of the minute spot 80 and the water-repellent function of the glass surface. Thus, the center of the minute spot 80 can be positioned at the prescribed position. In this arrangement, even when the part of the minute spot 80 contacts with the glass surface, no trace after the movement of the sample solution is formed, because the glass surface is water-repellent. The shape of the spot after the immobilization is determined by only the hydrophilic portion. Thus, the dispersion of the shape is reduced.

Figure 19B:
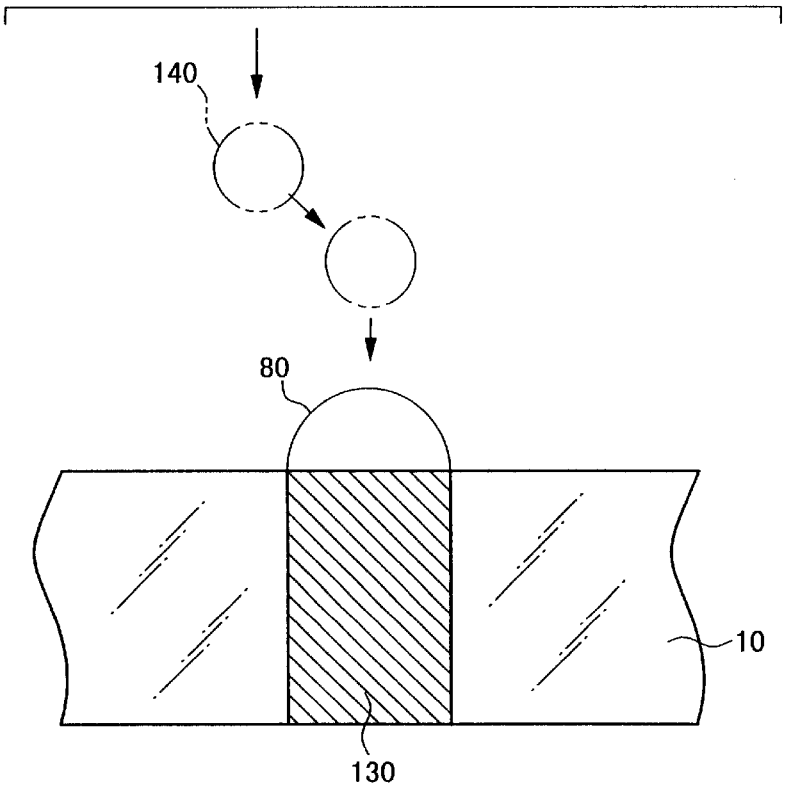
FIG. 19B illustrates the fact that an effect equivalent to that obtained in the sixth modified embodiment is obtained by using the positional deviation-correcting means according to the eighth modified embodiment.

When the intensity of the electric field is increased, as shown in FIG. 19B, the liquid droplet 140, which is in the falling process, is corrected for its traveling direction in the air so that the traveling direction is directed toward the corresponding electrode pattern 130, in the same manner as in the sixth modified embodiment described above. The minute spot 80 based on the liquid droplet 140 correctly falls onto the corresponding electrode pattern 130. In this case, the liquid droplet 140 is not moved on the surface of the base plate 10. Therefore, an effect is obtained such that no trace is formed by the movement of the liquid droplet, and it is possible to obtain a stable (uniform) shape of the spot.

As described above, both of the effects of the first modified embodiment and the sixth modified embodiment described above are simultaneously exhibited in the eighth modified embodiment which is more preferred. The material for the base plate 10 is not limited to glass, which may be an insulating matter such as ceramics and plastic.

As described above, even in the case of the use of the positional deviation-correcting means according to the first to eighth modified embodiments, the arrangement state of the large number of minute spots 80 formed on the base plate 10 can be the state which conforms the prescribed arrangement pitch, even when any dispersion occurs in the deviation width of the dispenser 30 and the arrangement pitch of the sample discharge ports 54, in the same manner as in the embodiment according to the present invention described above. Thus, it is possible to improve the quality of the DNA chip 20 and improve the yield.

It is a matter of course that the DNA chip and the method for producing the same according to the present invention are not limited to the embodiments described above, which may be embodied in other various forms without deviating from the gist or essential characteristics of the present invention.

What is claimed is:

1. A DNA chip comprising a plurality of sample spots comprising DNA supplied on a base plate, wherein:

said base plate is provided with positional deviation-correcting means for displacing said plurality of sample spots and automatically correcting any positional deviation of each of said plurality of sample spots after said sample spots are supplied on said base plate, said base plate comprising a plurality of said sample spots at correct positions, wherein said positional deviation-correcting means comprises at least one pointed projection positioned on said base plate, said at least one projection being centered at a correct position for each of said plurality of sample spots supplied on said base plate.

2. A method for producing a DNA chip comprising a plurality of sample spots comprising DNA supplied on a base plate, comprising the steps of:

providing a base plate having positional deviation-correcting means for displacing said plurality of sample spots and automatically correcting any positional deviation of each of said plurality of sample spots after said sample spots are supplied on said base plate;

supplying said plurality of sample spots onto said base plate; and correcting any positional deviation of each of said plurality of sample spots, wherein said positional deviation-correcting means comprises at least one pointed projection positioned on said base plate, said at least one pointed projection being centered at a correct position for each of said plurality of sample spots supplied on said base plate.

3. The method for producing said DNA chip according to claim 2, wherein said step of supplying said plurality of spots on said base plate is performed with an ink-jet system using a supply apparatus.

4. The method for producing said DNA chip according to claim 3, wherein said supply apparatus is a dispenser comprising a plurality of arranged micropipettes each including a pouring port for pouring a sample solution from outside, a cavity for pouring and charging said sample solution thereinto, and a discharge port for discharging said sample solution thereby providing said plurality of sample spots on said base plate, said micropipette further including a piezoelectric/electrostrictive element disposed on at least one wall surface of said substrate forming said cavity to operate as a means for moving said sample solution through said cavity, the method further comprises the step of discharging mutually different types of said sample solutions from said discharge ports of said micropipettes.

5. The method for producing said DNA chip according to claim 4, wherein said sample solution moves in a laminar flow within said cavity in said dispenser comprising said plurality of arranged micropipettes.

* * * * *